United States Patent
Riek et al.

(10) Patent No.: US 9,486,130 B2
(45) Date of Patent: Nov. 8, 2016

(54) TROCAR SYSTEM

(76) Inventors: Siegfried Riek, Rottweil (DE);
Karl-Heinz Bachmann, Villingendorf (DE); Thomas Gaiselmann, Villingendorf (DE)

( * ) Notice: Subject to any disclaimer, the term of this patent is extended or adjusted under 35 U.S.C. 154(b) by 25 days.

(21) Appl. No.: 14/129,897

(22) PCT Filed: Jun. 4, 2012

(86) PCT No.: PCT/EP2012/002354
§ 371 (c)(1),
(2), (4) Date: Dec. 27, 2013

(87) PCT Pub. No.: WO2013/000537
PCT Pub. Date: Jan. 3, 2013

(65) Prior Publication Data
US 2014/0148655 A1     May 29, 2014

(30) Foreign Application Priority Data

Jun. 30, 2011   (DE) .................. 10 2011 107 613

(51) Int. Cl.
*A61B 17/70*   (2006.01)
*A61B 1/313*   (2006.01)
(Continued)

(52) U.S. Cl.
CPC ........... *A61B 1/313* (2013.01); *A61B 1/00087* (2013.01); *A61B 17/29* (2013.01);
(Continued)

(58) Field of Classification Search
CPC .. A61B 1/018; A61B 1/012; A61B 1/00087; A61B 1/00096
USPC ........ 600/249, 106, 129, 156, 160, 171, 176
See application file for complete search history.

(56) References Cited

U.S. PATENT DOCUMENTS 5,354,302 A * 10/1994 Ko ..................... A61B 1/00087
600/158
5,632,717 A *  5/1997 Yoon .................. A61B 1/00082
600/104

(Continued)

FOREIGN PATENT DOCUMENTS

WO           0101847 A1     1/2001

OTHER PUBLICATIONS

Patent Cooperation Treaty, "International Search Report" European Searching Authority, document of 5 pages, Sep. 27, 2012.

(Continued)

*Primary Examiner* — Ellen C Hammond
*Assistant Examiner* — Stuart S Bray
(74) *Attorney, Agent, or Firm* — Akerman LLP; Peter A. Chiabotti

(57) ABSTRACT

A trocar system, comprising a trocar having an optical channel extending coaxially in the trocar for receiving an optical unit, and a hollow transparent distal tip of the trocar, which can be observed from the interior. The distal working end of an instrument having two working parts movable relative to one another is formed on the distal tip, wherein a first working part is an integral component of the tip and the second working part is mounted movably on the tip, wherein an actuating channel is constructed in the wall of the trocar surrounding the optical channel, which channel extends axially parallel from the proximal end of the trocar into the distal tip thereof, and wherein an actuating element is received in the actuating channel such as to be axially displaceable.

18 Claims, 1 Drawing Sheet

(51) Int. Cl.
*A61B 1/00* (2006.01)
*A61B 1/018* (2006.01)
*A61B 17/29* (2006.01)
*A61B 17/34* (2006.01)
*A61B 17/00* (2006.01)

(52) U.S. Cl.
CPC .......... *A61B 17/34* (2013.01); *A61B 17/3417* (2013.01); *A61B 1/018* (2013.01); *A61B 2017/00353* (2013.01); *A61B 2017/00907* (2013.01); *A61B 2017/2932* (2013.01); *A61B 2017/2933* (2013.01); *A61B 2017/3445* (2013.01); *A61B 2017/3454* (2013.01); *A61B 2090/3614* (2016.02); *F04C 2270/0421* (2013.01)

(56) References Cited

U.S. PATENT DOCUMENTS

| | | | | |
|---|---|---|---|---|
| 5,685,820 A * | 11/1997 | Riek | A61B 1/00165 | 600/104 |
| 6,183,485 B1 * | 2/2001 | Thomason | A61B 17/0469 | 606/139 |
| 7,604,648 B2 * | 10/2009 | Kerr | A61B 17/0206 | 606/15 |
| 2004/0225305 A1 * | 11/2004 | Ewers | A61B 1/00135 | 606/153 |
| 2005/0096502 A1 * | 5/2005 | Khalili | A61B 1/018 | 600/106 |
| 2005/0234294 A1 * | 10/2005 | Saadat | A61B 1/0008 | 600/104 |
| 2006/0178556 A1 * | 8/2006 | Hasser | A61B 1/05 | 600/102 |
| 2006/0282098 A1 * | 12/2006 | Shelton | A61B 1/00087 | 606/144 |
| 2007/0129719 A1 * | 6/2007 | Kendale | A61B 1/00096 | 606/41 |
| 2007/0135803 A1 * | 6/2007 | Belson | A61B 1/00154 | 606/1 |
| 2008/0103439 A1 * | 5/2008 | Torrance | A61B 17/3207 | 604/93.01 |
| 2008/0147002 A1 | 6/2008 | Gertner | | |
| 2008/0275300 A1 * | 11/2008 | Rothe | A61B 1/0008 | 600/129 |
| 2008/0287740 A1 * | 11/2008 | Weitzner | A61B 17/3417 | 600/139 |
| 2009/0024156 A1 * | 1/2009 | Chin | A61B 17/00008 | 606/194 |
| 2009/0143643 A1 * | 6/2009 | Weitzner | A61B 1/00135 | 600/106 |
| 2009/0149716 A1 * | 6/2009 | Diao | A61B 1/00085 | 600/202 |
| 2009/0163768 A1 * | 6/2009 | Ibrahim | A61B 17/3421 | 600/106 |
| 2010/0152612 A1 * | 6/2010 | Headley, Jr. | A61B 10/04 | 600/566 |
| 2010/0228085 A1 * | 9/2010 | Mirza | A61B 1/018 | 600/106 |
| 2010/0262140 A1 * | 10/2010 | Watson | A61B 1/0008 | 606/41 |
| 2011/0112434 A1 * | 5/2011 | Ghabrial | A61B 1/00135 | 600/564 |
| 2011/0130779 A1 * | 6/2011 | Mirza | A61B 1/018 | 606/170 |
| 2011/0152610 A1 * | 6/2011 | Trusty | A61B 1/0008 | 600/104 |
| 2011/0207997 A1 * | 8/2011 | Greenburg | A61B 5/05 | 600/104 |
| 2012/0289858 A1 * | 11/2012 | Ouyang | A61B 10/0275 | 600/562 |
| 2013/0102843 A1 * | 4/2013 | Feuer | A61B 1/00087 | 600/109 |
| 2014/0128671 A1 * | 5/2014 | Riek | A61B 1/018 | 600/104 |
| 2014/0228643 A1 * | 8/2014 | Possover | A61N 1/0558 | 600/160 |
| 2015/0032024 A1 * | 1/2015 | Furlong | A61B 17/221 | 600/563 |
| 2015/0045675 A1 * | 2/2015 | Chernomorsky | A61M 29/02 | 600/471 |
| 2016/0174814 A1 * | 6/2016 | Igov | A61B 1/0051 | 600/106 |
| 2016/0175006 A1 * | 6/2016 | Dejima | A61B 1/00112 | 600/114 |

OTHER PUBLICATIONS

Patent Cooperation Treaty, Translation of "Written Opinion" European Search Authority, document of 5 pages, Dec. 31, 2013.

* cited by examiner

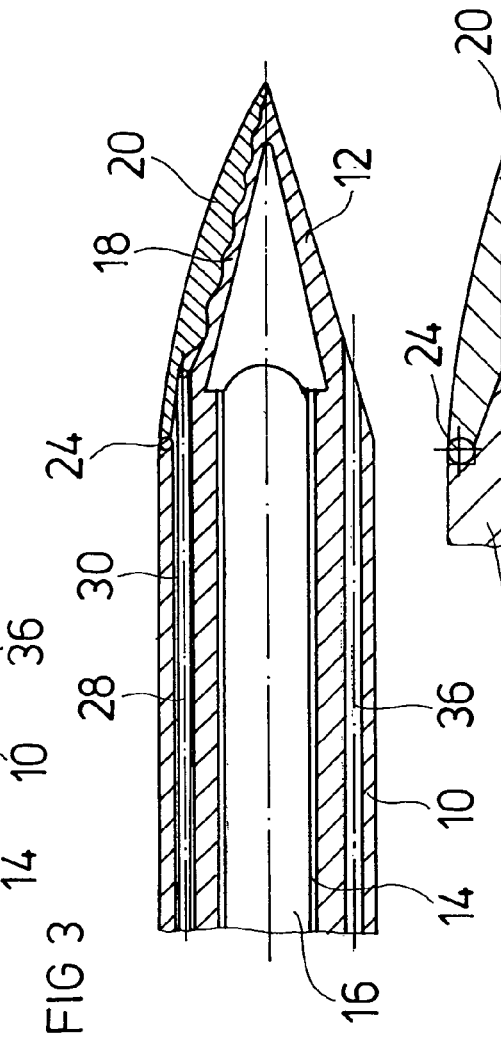

TROCAR SYSTEM

CROSS REFERENCE TO RELATED APPLICATIONS

This application is a §371 National Phase of PCT/EP2012/002354, filed Jun. 4, 2012, which claims priority to German Patent Application No. 10 2011 107 613.5, filed Jun. 30, 2011, the entireties of which are incorporated by reference herein.

BACKGROUND

The application relates to a trocar system.

SUMMARY

Trocar systems that are intended for use in minimally invasive surgical applications typically consist of a trocar that is used to create an opening in a body cavity (for example, the abdomen) and a trocar sleeve that is placed and remains inside said opening constituting an access point to the inside of the body cavity for the surgical procedure. The trocar includes a distal tip for penetrating the body tissues, for example the abdominal wall, and serves to create an opening. The tip of the trocar can be configured as pointed, cutting or dull. A pointed tip, for example, has the shape of a three-edged pyramid. Cutting tips include a blade for a tissue incision that is subsequently dilated by a cone-shaped tip. Dull tips are distally rounded, which means that very high penetration pressures must be applied to them if they are used for opening up tissue layers. Correspondingly, dull tips are essentially only used to dilate a previously created lesion.

These trocars, particularly pointed and cutting trocars, are associated with risks; upon penetrating the abdominal wall, they may cause injury to internal organs that can adhere to the peritoneum due to internal adhesions, such as, for example, the bowel and/or blood vessels in the abdominal wall or retroperitoneum. To reduce this risk, so-called optical trocars are in use, for example, as disclosed in U.S. Pat. No. 5,685,820 A. The distal tip on these optical trocars is configured as a hollow, transparent cone that can be observed from the inside through an optical unit, which is taken up inside an optical channel extending coaxially inside the trocar. With the transparent tip, the optical trocar gives access to a three-dimensional view of the tissue layers of the abdominal wall through which the trocar passes. This affords the surgeon with a sensed idea for the motion, speed and position of the trocar tip during penetration. In particular, it is possible to detect any adhesions that may be present between the bowel and the peritoneum at the insertion point prior to penetrating the peritoneum. Nevertheless, the high penetration pressures needed for passing through the fascia and the peritoneum still remain problematic. Although, conceivably, it is possible to reduce the necessary penetration pressures by the use of cutting blades that are disposed on the trocar tip, the use of a blade poses new injury risks for the bowel during the penetration step. Still, when the known trocar is used with or without cutting edge for penetrating the abdominal wall, relatively high pressures and a rotating motion of the trocar are necessary. There results the so-called tenting effect, whereby the trocar presses the tissue layers that require high penetration pressures in a tent-like fashion into the abdomen, possibly advancing them into close proximity of the retroperitoneum. When these layers are opened, they give way to the penetration pressure suddenly, and the tip penetrates the abdomen all of a sudden, possibly making it difficult for the surgeon to control the sudden trocar motion in an effort to avoid injuring internal organs or large vessels in the retroperitoneum with the tip of the trocar. To reduce this problem, many surgeons work with trocars that are equipped with blunt tips. This procedure envisions first the placement of a skin incision, in the manner of an open laparotomy, through the abdominal wall, which is then only dilated with the blunt-tip optical trocar, and whereby the tip of the trocar is not effectively used for penetrating the tissue. However, the open incision in the abdominal wall is in contradiction of the stated goal of a minimally invasive surgical technique.

Therefore, the present disclosure provides a trocar system that utilizes the advantages of the optical trocar, improves safety during tissue penetration and allows for preparation inside the tissue.

This object is achieved by a trocar system having the features and structures disclosed therein.

Advantageous embodiments are indicated in the dependent claims.

The disclosure provides for using the trocar not only as a passive tool that is manually guided by an axial force and, if necessary, a rotational movement through the tissue layers. Rather, the trocar can be actively used as an instrument that facilitates the penetration of tissue layers by means of the distal tip, rendering it safer and allowing, in particular, for the implementation of preparation steps with the trocar inside the tissue. To this end, the working end of an instrument is configured at the distal tip of the trocar, which can be optically observed from the inside, and wherein said working end includes two working parts that are movable relative to each other. One of these working parts is an integral component of the tip, while the second working part is movably supported on the tip and can be moved, using an actuation element, relative to the tip, and thereby relative to the first working part. The actuating element is guided in an axially movable fashion inside the actuating channel, which is formed inside the trocar.

When perforating the tissue with the trocar, the working end that is disposed at the distal tip can be actuated, if necessary, in order to implement surgical steps that facilitate the penetration of the respective tissue layer, or that are suited for other kinds of surgical preparation. Due to the fact that the first working part is an integral component of the transparent distal tip of the trocar, the working end and the functionality thereof can be directly observed by means of the optical unit of the optical trocar, such that the surgeon is able to actuate the working end while having visual contact, and therefore, working with minimal risk. The movable second working part can also be transparent, if necessary.

The working end can be configured in various forms, corresponding to the different surgical instruments. In one embodiment, the working end is configured in the manner of a pair of forceps with two jaws. The one jaw is formed by the transparent wall of the distal tip of the trocar, while the other tip is formed by the movable second working part.

The working end of the instrument can be configured as a pair of forceps or as a clamp. Further, the working end can be configured as a pair of scissors, as a dissector or as a coagulation forceps. A bipolar high-frequency electrical design is possible for coagulation and/or sectioning. A configuration with high-frequency ultrasonic vibrations is also possible.

In one configuration as a pair of forceps, it is possible to grip and hold the tissue resting against the distal tip of the trocar, whereby it is possible to separate and open the respective tissue layer, for example, by means of a blade or a pair of scissors. A blade or a pair of scissors of this kind can be preferably guided through an additional working channel toward the distal tip of the trocar. In one embodiment of the working element as a coagulation forceps and/or dissector, preparation of the tissue and, if necessary, the coagulation of vessels by means of the trocar itself is possible. Correspondingly, the application of a trocar has been expanded beyond merely creating an access point for minimally invasive surgery, because now the trocar system can also be used for surgical preparation work.

If the working end is configured in the manner of a pair of forceps, the movable working part is preferably pivotably disposed on the distal tip of the trocar. The first working part is preferably formed by a flatness or depression in the exterior surface of the distal tip. When the working end is in the closed state, the movable working part places itself into this flatness or depression, such that the movable working part inserts itself completely in the exterior circumferential contour of the distal tip and does not interfere with the tissue dilatation, when the tip of the trocar penetrates the tissue.

In another embodiment, the second working part can be guided as linearly displaceable inside the exterior jacket area of the distal tip of the trocar. In this case, it is possible for the distal end of the movable second working part to interact with a stop edge on the exterior surface of the distal tip to make a punching or cutting procedure possible. The movable working part therein is preferably guided inside a groove of the exterior jacket surface of the distal tip, particularly in such a manner that, here too, the second working part inserts itself into the exterior contour of the distal tip.

The movable working part is actuated by means of the actuating element that the surgeon operates at the proximal end or that is connected to an ultrasonic generator, if necessary. The actuating element engages by the distal end thereof with the movable working part. To actuate the movable working part in both directions, such as, for example, for opening and closing the clamp, the actuating element must have a sufficient measure of longitudinal rigidity. The actuating element can engage at the movable working part via a point-type fulcrum. Due to the fact that, when the second working part moves, this fulcrum point does not move along a path that is exactly axially parallel, in this configuration, the actuating element can be elastically deflected from the axially parallel straight form at the distal end. In another configuration, the distal end of the actuating element engages in a sliding bock guide of the second working part, which is disposed as inclined relative to the axial direction.

BRIEF DESCRIPTION OF THE DRAWINGS

The features and structures of the present disclosure will be described in further detail below based on a single embodiment that is illustrated in the drawings. Shown are as follows:

FIG. 1 is a representation of an axial section of the distal end of the trocar of the trocar system in the open position of the working end;

FIG. 2 is a representation of an axial view onto the distal end in the position as depicted in FIG. 1;

FIG. 3 is a representation of an axial section corresponding to the one in FIG. 1 with the working end in the closed position;

FIG. 4 is a representation of an axial view onto the distal end according to FIG. 3; and FIG. 5 is a representation of an enlarged partial section of the articulation of the actuating element to the movable working part.

DETAILED DESCRIPTION OF THE ILLUSTRATED EMBODIMENTS

The trocar system includes a trocar that serves for penetrating the tissue layers, for example, of the abdominal wall. Using the trocar, an access opening is created to the interior of the body, for example to the abdominal cavity. The trocar system can additionally include a trocar sleeve that is inserted by means of the trocar into the body opening, remains in the thus created opening and is used, after the trocar has been removed, as an access point for a minimally invasive surgery.

The drawing and the subsequent description only address the distal end of the trocar, where the invention is embodied. The further parts of the trocar system correspond to the known prior art, which is why they do not require further description and detailed explanation.

The trocar 10 of the trocar system has the shape of a rigid circular cylinder that is made of metal or plastic. The distal tip 12 of the trocar is substantially cone-shaped and typically includes a blunt, rounded tip. The jacket area can also be slightly convexly arched.

The tip 12 is hollow on the inside and is made of a transparent plastic material. An optical channel 14 extends coaxially along the interior of the trocar 10, where an optical unit 16, such as, for example, a rod-lens optics means or a camera chip can be inserted, if necessary, with an integrated illumination system. The optical unit 16 is inserted in such a manner that the distal end thereof is disposed approximately in the base area of the cone-shaped tip 12. Using the optical unit 16, it is possible to illuminate the transparent tip 12 of the trocar from the inside and observe the area. This way, the surgeon is afforded the opportunity of observing the tissue that rests against the exterior of the transparent tip 12 and how the tip 12 advances through the tissue. Up to this point, the trocar system, and particularly the trocar 10, is compliant with the optical trocar that is known from the prior art.

The distal working end of the surgical instrument is configured at the distal tip 12 of the trocar 10. This working end consists of a working part 18 and a second working part 20 that interacts with the former. The first working part 18 is an integral component of the distal tip 12 of the trocar 10. This means that the first working part 18 is formed from the transparent plastic material of the tip 12 of the trocar. The second working part 20 is movably disposed on the exterior of the distal tip 12, specifically in such a manner that the second working part 20 can be moved in relation to the first working part 18. The second working part 20 is also preferably made of a transparent plastic material.

In terms of form and functionality, the working parts 18 and 20 can substantially correspond to the working parts of known surgical instruments. This means that the interacting areas of the first working part 18 and of the second working part 20 can have different shapes. The shown embodiment depicts the distal working end in form of a clamp having two jaws that can be moved in relation to each other only by way of an example and is not intended to limit the scope of the disclosure in any way. Embodiments as coagulation forceps, dissector, etc. result by analogy.

In the shown embodiment, the first working part 18 is configured as a depression that is formed inside the exterior jacket surface of the tip 12. The depression extends in a jacket line of the cone-shaped tip 12 substantially from the base of the tip 12 to the distal tip of the cone. The base of the depression of the first working part 18 includes a corrugated area 22 to facilitate gripping and grasping of the tissue.

The second working part 20 is configured as a jaw in the shown embodiment, which is pivotably disposed by means of a joint 24 on the trocar 10 by the proximal end thereof. The joint 24 is disposed approximately at the transition location of the distal tip 12 and the cylindrical area of the trocar 10. The second working part 20 extends from the joint 24 to the distal crown of the tip 12. The cross-sectional form of the second working part 20 is complementary to the form of the depression of the first working part 18. At the edge thereof, that engages in the depression of the first working part 18, the second working part also includes a corrugated area 26.

The second working part 20 can be pivoted about the joint 24 into one of the open positions, as shown in FIGS. 1 and 2. In this open position, the second working part 20 is pivoted out of the depression of the first working part 18, causing the first working part 18 and the second working part 20 to open in the distal direction in the manner of a pair of scissors. From this open position, the second working part 20 can be pivoted into the closed position, as shown in the FIGS. 3 and 4. In said closed position, the second working part 20 inserts itself, congruently to shape, into the depression of the first working part 18. The second working part 20 now completely fills out the depression of the first working part, and the exterior surface of the second working part 20 completely inserts itself into the cone-shaped jacket surface of the tip 12. The corrugated area 22 of the first working part 18 and the corrugated area 26 of the second working part 20 engage in each other.

The actuating element 28 serves for pivoting the second working part 20. The actuating element 28 is received in an actuating channel 30 that is formed in the wall of the trocar 10. The actuating channel 30 extends axially parallel inside the trocar 10 from the proximal end thereof to the distal tip 12. The actuating channel 30 can be formed as a bore inside the wall of the trocar 10, as depicted in the embodiment. In the same way, it is possible for the actuating channel 30 to be configured as a groove in the exterior jacket surface of the trocar 10. The actuating element 28 is configured as a thin rod that is guided, axially displaceable, inside the actuating channel 30. At the proximal end, which is not shown, the actuating element 28 protrudes from the actuating channel 30, and thereby from the trocar 10, whereby the surgeon is able to operate the actuating element 28 by means of a suitable handle element. The distal end of the actuating element 28 engages at the second working part 20 in order to pivot the same about the joint 24 between the open position and the closed position. To allow for active pivoting in both pivoting directions, the actuating element 28 includes a sufficient amount of longitudinal rigidity.

In the shown embodiment, as depicted particularly in FIG. 5, the actuating element 28 engages by a transverse pin 32, which is formed at the distal end thereof, in a sliding bock guide 34 that is configured in the second working part 20. The sliding bock guide 34 is configured as a slot that is disposed as inclined relative to the longitudinal axis of the trocar. When the actuating element 28 is retracted in the proximal direction, the transverse pin 32 runs against the proximal end of the sliding bock guide 34, as depicted in FIGS. 3 and 5, whereby the second working part 20 is pulled into the closed position. When the actuating element 28 is advanced in the distal direction, the transverse pin 32 is displaced in the sliding bock guide 34 in the distal direction, and the second working part 20 is pressed in the open position, as shown in FIG. 1.

In an alternate embodiment, which is presently not shown in the drawings, it is possible for the actuating element 28 to be articulated in a point-like fashion with the second working part 20. Due to the fact that the point of articulation is slightly moved along a circle arc, when the second working part 20 performs the pivoting movement, in this embodiment, the actuating element 28 has a small measure of elastic flexibility, whereby the distal end of the actuating element 28, which exits from the actuating channel 30, is able to follow this small angular movement.

In the embodiment that is depicted in the drawing, the second working part 20 is pivotably supported to the first working part 18 at the distal tip 12. In a further configuration, which is presently not shown, the second working part can also be supported, linearly displaceable, in a jacket line of the tip 12 on the exterior of the tip 12. In this case, the first working part is formed as a stop edge on the exterior of the tip 12. Using an actuating element, it is possible for the second working part to be displaced, linearly guided, in the distal direction, whereby the distal end thereof interacts with the stop edge of the first working part in the manner of a punch. The same opens up, when the actuating element pulls the second working part in the proximal direction and in the open position.

Aside from the actuating channel 30, at least one working channel 36 is preferably formed in the trocar system that extends from the proximal end to the distal end of the trocar. A working channel 36 is diametrically disposed relative to the actuating channel 30 in the depicted embodiment. A miniature instrument can be guided through the working channel 36, and the working end of which protrudes distally from the working channel 36 at the distal tip 12. The miniature instrument can be, for example, a pair of scissors, a blade, a coagulation instrument, a miniature camera, a fiber-optic light guide, an illumination system, an optical unit, or the like. As depicted in the drawing, the working channel 36 can be configured inside the trocar 10. Alternately, the working channel can extend inside a trocar sleeve that encloses the trocar, or it can extend between the trocar 10 and the trocar sleeve. Working channels of this kind can serve not only for introducing miniature instruments but also, for example, as rinsing channels.

When a tissue layer is reached during the tissue penetration procedure, for example in connection with penetrating an abdominal wall, that offers greater resistance, for example the fascia of the peritoneum, it is possible to hold the tissue by the clamping means, which is formed of the working parts 18 and 20, at the tip of the distal tip 12 of the trocar 10 and then cut into the tissue with a miniature instrument that is introduced through the working channel 36, whereby the further penetration of the trocar tip is facilitated.

When the working element is configured as a dissector, the tissue layers, for example fascia or peritoneum, can be opened also via preparation of the area by the working end itself, which is configured on the tip 12 of the trocar 10. If the working end can be actuated by electrical or high-frequency vibrations, it is also possible to implement coagulation during the preparation, if necessary.

LIST OF REFERENCE SIGNS

10 Trocar
12 Tip

14 Optical channel
16 Optical unit
18 First working part
20 Second working part
22 Corrugated area of 18
24 Joint
26 Corrugated area of 20
28 Actuating element
30 Actuating channel
32 Transverse pin
34 Sliding bock guide
36 Working channel

The invention claimed is:

1. A trocar system, comprising:
a rigid trocar, having an optical channel that extends coaxially inside the trocar for receiving an optical unit, the trocar having a hollow transparent distal tip in the shape of a cone and through which an area outside of the distal tip can be observed from an interior by the optical unit,
wherein a distal working end of an instrument is configured at the distal tip,
wherein the instrument includes at least two working parts that can be moved relative to each other,
wherein a first of the at least two working parts is an integral component of the distal tip and the second of the at least two working parts is separate from the distal tip and disposed on the exterior of the distal tip and is movably supported on the distal tip,
wherein the hollow transparent distal tip remains closed when the second of the at least two working parts is moved,
wherein an actuating channel is configured on the trocar and leads from a proximal end of the trocar to the distal tip, and
wherein an actuating element is received in an axially displaceable manner inside the actuating channel, and a proximal end of the actuating element is guided out from a proximal end of the actuating channel, and the distal end of the actuating element engages on the second working part in order to move the second working part, and
wherein a working channel is provided in a wall of the trocar and the working channel opens at the distal tip and exterior to the distal tip.

2. The trocar system according to claim 1,
wherein the first working part is integrated in a wall of the distal tip of the trocar.

3. The trocar system according to claim 1,
wherein the second working part is pivotably supported at the distal tip of the trocar between an open position and a closed position.

4. The trocar system according to claim 3,
wherein the first working part is a depression in an exterior surface of the distal tip, and wherein, in the closed position, the second working part inserts itself in a complementary manner into the depression.

5. The trocar system according to claim 1,
wherein the second working part is supported in a linearly displaceable manner in a jacket line of the distal tip, and wherein the second working part interacts with a stop edge that is configured as a first working part in the distal tip.

6. The trocar system according to claim 1,
wherein the actuating element is longitudinally rigid.

7. The trocar system according to claim 6,
wherein the actuating channel comprises an axially parallel bore inside a wall of the trocar or as an axially parallel groove in an exterior jacket surface of the trocar, and wherein the actuating element is rod-like and guided as axially displaceable in the actuating channel.

8. The trocar system according to claim 1,
wherein the actuating element engages by the distal end thereof in a sliding block guide of the second working part, which is disposed as inclined relative to an axis of the trocar.

9. The trocar system according to claim 1,
wherein the actuating element is rotatably articulated in a point arrangement by the distal end thereof to the second working part.

10. The trocar system according to claim 1, further comprising an axially continuous working channel for passing a miniature instrument, an optical unit, a fiber-optic light guide or an illumination system there through.

11. The trocar system according to claim 1, wherein the distal working end of the instrument is configured as a clamp, as a pair of forceps, as a pair of scissors, as a dissector or as a coagulation forceps.

12. The trocar system according to claim 1, further comprising an axially continuous working channel that functions as a rinsing channel.

13. A trocar system, comprising:
a rigid trocar with a hollow transparent distal tip;
an optical channel that extends inside the rigid trocar for receiving an optical unit and terminates inside the hollow transparent distal tip;
a working channel in a wall of the rigid trocar that opens proximate to the hollow transparent distal tip and exterior to the hollow transparent distal tip;
an instrument located at the hollow transparent distal tip, the instrument including a plurality of working parts that can be moved relative to each other, wherein a first working part of the plurality of working parts is an integral component of the hollow transparent distal tip and a second working part of the plurality of working parts is located exterior to the hollow transparent distal tip, separate from the hollow transparent distal tip, and movably supported on the hollow transparent distal tip such that the hollow transparent distal tip remains closed when the second working part of the plurality of working parts is moved;
an actuating channel leading from a proximal end of the rigid trocar to the hollow transparent distal tip; and
an axially displaceable actuating element inside the actuating channel that engages the second working part of the plurality of working parts to move the second working part of the plurality of working parts.

14. The trocar system according to claim 13,
wherein the first working part of the plurality of working parts is integrated in a wall of the hollow transparent distal tip of the rigid trocar.

15. The trocar system according to claim 14,
wherein the first working part of the plurality of working parts is transparent.

16. The trocar system according to claim 15,
wherein the second working part of the plurality of working parts is transparent.

17. The trocar system according to claim 13,
wherein the first working part of the plurality of working parts is a depression in an exterior surface of the hollow transparent distal tip, and in a closed position, the second working part of the plurality of working parts fits in the depression.

18. The trocar system according to claim 13,
wherein the first working part of the plurality of working parts is a stop edge on the exterior of the hollow transparent distal tip and the second working part of the plurality of working parts is located in a jacket line of the distal tip and linearly displaceable therefrom to interact with the stop edge as a punch.

\* \* \* \* \*